United States Patent [19]

Dreher et al.

[11] Patent Number: 5,132,226
[45] Date of Patent: Jul. 21, 1992

[54] METHOD FOR THE DETERMINATION OF MALEIMIDE GROUPS

[75] Inventors: Michael Dreher; Heinz Hirsch, both of Weiterstadt, Fed. Rep. of Germany

[73] Assignee: Merck Patent Gesellschaft Mit Beschrankter Haftung, Darmstadt, Fed. Rep. of Germany

[21] Appl. No.: 451,708

[22] Filed: Dec. 18, 1989

[30] Foreign Application Priority Data

Dec. 19, 1988 [DE] Fed. Rep. of Germany ....... 3842657

[51] Int. Cl.$^5$ ............................................ G01N 33/53
[52] U.S. Cl. ..................... 436/86; 436/106; 436/96; 436/172; 431/512; 431/546
[58] Field of Search ................... 436/86, 106, 96, 120, 436/164, 172, 512, 546, 547

[56] References Cited

U.S. PATENT DOCUMENTS 4,615,986 10/1986 Yoshida ............................... 436/500
4,722,893 2/1988 Shigetu et al. ......................... 435/7
4,847,376 7/1989 Neumann et al. .................... 544/102

Primary Examiner—David L. Lacey
Assistant Examiner—N. Edwards
Attorney, Agent, or Firm—Millen, White & Zelano

[57] ABSTRACT

A method and an agent for the determination of maleimide groups, comprising reacting a sample containing maleimide groups with a reagent containing thiol groups and then with a chromogen or fluorogen which reacts with thiol groups, and measuring the change in intensity.

8 Claims, No Drawings

METHOD FOR THE DETERMINATION OF MALEIMIDE GROUPS

BACKGROUND OF THE INVENTION

The invention relates to a method and an agent for the determination of maleimide groups and in particular for the determination of reactive maleimide groups bonded to proteins, e.g., enzymes, antigens and antibodies.

Since the mid-1970's, many so-called heterocrosslinkers have been developed for the purpose of covalently bonding proteins together via different reactive groups, e.g., amino groups, carboxyl groups, hydroxyl groups and thiol groups. These heterocrosslinkers have become of particular interest in the area of immunoassay reagents. Heterocrosslinkers carrying maleimide groups may be specially singled out here because they have the property of reacting specifically with thiol groups. Thus, antibody fragments, e.g., Fab' fragments, containing free thiol groups can be selectively bonded to other proteins, e.g., enzymes.

Examples of such crosslinkers and heterocrosslinkers carrying maleimide groups are succinimidyl m-maleimidobenzoate (SMB), sulfosuccinimidyl m-maleimidobenzoate (sulfo-SMB), succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), succinimidyl 4-(p-maleimidophenyl)butyrate (SMPB), sulfosuccinimidyl 4-(p-maleimidophenyl)butyrate (sulfo-SMPB), bis-maleimidohexane (BMH), N-(4-diazophenyl)maleimide and N-($\beta$-diazophenylethyl)maleimide.

Thiol groups can be bonded to amino groups with the aid of these heterocrosslinkers. Furthermore, N-(4-diazophenyl)maleimide and N-($\beta$-diazophenylethyl)maleimide also make it possible to bond thiol groups to imidazole, phenol, indole and other groups.

In principle, these reactions take place according to the following scheme:

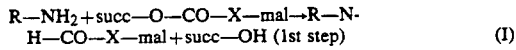
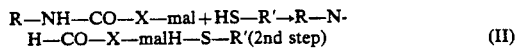

wherein R—NH$_2$ = a protein-carrying primary amino groups; mal = a maleimide group; succ = a succinimidyl group; R'—SH = a protein-carrying thiol group; and X = a spacer.

SUMMARY OF THE INVENTION

Surprisingly, it has been found that to prepare effective immunoassay reagents, it is crucial to know the number and functionality of the maleimide groups bonded to the spacer in intermediate I of the above equation, before the reaction with, e.g., antibody fragments, is carried out. This make it possible to avoid the costintensive preparation of ineffective products.

The present invention provides a method and an agent which make it possible to detect the number of functional reactive maleimide groups in intermediate I above.

The invention relates to a method for the determination of maleimide groups which is characterized in that a sample containing maleimide groups is reacted with a reagent containing thiol groups and then with a chromogen or fluorogen which reacts with thiol groups, and the change in intensity of the chromogen or fluorogen is measured.

The invention further relates to an agent for the determination of maleimide groups which comprises a reagent containing thiol groups and a chromogen or fluorogen which reacts with thiol groups.

The direct determination, with chromogens or fluorogens, of maleimide groups bonded to proteins requires a chromatographic separation. The method according to the instant invention, on the other hand, is carried out in a homogeneous, i.e., one-phase, procedure.

Maleimide groups are determined, e.g., by treating a solution of a protein-carrying maleimide groups with a solution of a mercaptoalkanol and incubating the mixture. A solution of a chromogen or fluorogen which reacts with thiol groups is then added. Excess mercaptoalkanol, i.e., mercaptoalkanol not bonded by the maleimide groups, causes the formation of a dye or a change in fluorescence, the intensity of which is measured. The method can be carried out either as an end point method or as a kinetic method, in which case the rate of formation of the dye or the rate of change of fluorescence is measured.

Suitable reagents containing thiol groups are all those compatible with the underlying chemistry and generally include compounds having thiol groups attached to aliphatic, aromatic and hydrocarbon moieties. Examples of suitable reagents containing thiol groups include, mercaptoalkanols such as mercaptoethanol and mercaptopropanol, mercaptoalkylamines such as cysteamine and mercaptopropylamine, mercaptoamino acids such as cysteine, and mercaptocarboxylic acids such as mercaptoacetic acid, mercaptosuccinic acid and 2-thiobenzoic acid, mercaptoethanol being preferred. The reagent containing thiol groups must be in 2-fold to 10-fold molar equivalent excess, preferably in 4-fold to 6-fold excess, relative to the number of maleimide groups on the protein carrying maleimide groups.

Suitable chromogens and fluorogens include, but are not limited to, all those which are known in the art for detecting thiol groups. For example, suitable chromogens are those which react with thiol groups, such as 2,2'-dinitro-5,5'-dithiodibenzoic acid, bis(p-nitrophenyl) disulfide and 2,2'-dipyridyl disulfide; 2,2'-dinitro-5,5'-dithiodibenzoic acid, which has long been known as Ellman's reagent (Arch. Biochem. Biophys. 82, 70 (1959)), is preferred. In a weakly basic medium (pH 8–9), the deep yellow 2-nitro-5-thiobenzoate is formed with Ellman's reagent by reductive cleavage of the disulfide bridge and its color intensity in the 400–450 nm region is a measure of the number of thiol groups. The concentration of the chromogen should be in the range from 0.1 to 1 mM, preferably 0.2 mM.

Examples of suitable fluorogenic substances are (o-nitroaniline-N-ethyldithio)-2-pyridyl-5-thioureido-N'-(5-fluorescein) and 4-iodoacetylamido-1-naphthol, preferably (o-nitroaniline-N-ethyldithio)-2-pyridyl-5-thioureido-N'-(5-fluorescein). In principle, the method proceeds analogously to that described by Ellman. Reaction of the fluorescein derivative with compounds containing thiol groups greatly increases the fluorescence of the fluorescein derivative. The fluorescence yield, relative to a standard, is a measure of the number of thiol groups. The concentration of the fluorogen should be in the range from 0.1 to 1 mM, preferably 0.2 mM.

The method and agent are generally suitable for the determination of maleimide or compounds containing maleimide groups. They are preferably suitable for determining the reactivity of immunoassay reagents containing maleimide groups, i.e., for the quality control of such reagents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, cited above and below, and of corresponding German application P 38 42 657.9, are hereby incorporated by reference.

EXAMPLES

Example 1

Determination of maleimide groups bonded to protein

A solution of horseradish peroxidase carrying maleimide groups (0.062 mM) is treated with a solution of mercaptoethanol. After an incubation time of 10 minutes, a solution of Ellman's reagent (2,2'-dinitro-5,5'-dithiodibenzoic acid) is added. Excess mercaptoethanol, i.e., mercaptoethanol not bonded by maleimide groups, causes the formation of the orange-yellow dye 2-nitro-5-thiobenzoate.

The color intensity is measured in a photometer at 436 nm and at room temperature. The color of the solution after the reaction is stable for at least one hour, so the measurement can be made as an end point measurement. The chosen dye has the advantage of absorbing at a wavelength where proteins are very unlikely to interfere. The analytical blank value is measured according to the pipetting scheme shown in Table 1.

TABLE 1

| | Standard | Standard Blank Value | Analysis | Analytical Blank Value |
|---|---|---|---|---|
| Solution 1 | 100 | 150 | — | 50 |
| Solution 2 | — | — | 100 | 100 |
| Solution 3 | 50 | — | 50 | — |
| | 10 minutes incubation at 37° C. | | | |
| Solution 4 | 2,500 | 2,500 | 2,500 | 2,500 |
| | After 10 minutes incubation, measure extinction at 436 nm against water | | | |
| | St | StB | A | AB |

The calculation is performed according to the following equation:

$$[(St-StB)-(A-AB)] \times 5 \text{ mM}/(St-StB) \times 2$$

Composition of the solutions:
Solution 1 = water
Solution 2 = analysis (substance carrying maleimide groups)
Solution 3 = standard (mercaptoethanol, 5 mM in degassed water)
Solution 4 = color reagent (Ellman's reagent, 0.2 mM in 0.05 M sodium borate +0.1% ascorbic acid, pH=8.0).

Example 2

Determination of the number (or concentration) of reactive maleimide groups in different crosslinkers and detection at different dilutions As many crosslinkers are poorly soluble in water, or the succinimidyl group is rapidly hydrolyzed by water, all substances are dissolved in dioxane.

Sample 1: 8.60 mg of succinimidyl 4-(p-maleimidophenyl)butyrate are dissolved in 9.65 ml of dioxane (2.5 mM).
Sample 2: 3.34 mg of succinimidyl m-maleimidobenzoate are dissolved in 4.25 ml of dioxane (2.5 mM).
Sample 3: 3.80 mg of bis-maleimidohexane are dissolved in 5.5 ml of dioxane (2.5 mM).

The test is carried out according to the pipetting scheme of Example 1.

The result is shown in Table 2 (in mM, % detection):

TABLE 2

| Sample 1 | | | Sample 2 | | | Sample 3 | | |
|---|---|---|---|---|---|---|---|---|
| Calc. | Meas. | % | Calc. | Meas. | % | Calc. | Meas. | % |
| 0.5 | 0.565 | 113 | 0.5 | 0.605 | 121 | 0.5 | 0.540 | 108 |
| 1.0 | 1.025 | 103 | 1.0 | 1.155 | 116 | 1.0 | 1.095 | 110 |
| 1.5 | 1.515 | 101 | 1.5 | 1.625 | 108 | | | |
| 2.0 | 2.005 | 100 | 2.0 | 2.135 | 107 | SH groups consumed | | |
| 2.5 | 2.475 | 99 | 2.5 | 2.490 | 100 | | | |

The result in this table clearly shows that even maleimide groups of different crosslinkers are correctly determined. The test is linear over a sufficiently large concentration range.

Example 3

Determination of the number (or concentration of maleimide groups in horseradish peroxidase 5.37 mg of horseradish peroxidase (HRP) carrying maleimide groups are dissolved in 1 ml of degassed water. Assuming a molecular weight of 45,000, this gives a concentration of 0.119 mM. This stock solution is diluted with degassed water in several steps: 1+4, 2+3, 3+2, 4+1. Measurement is carried out analogously to the pipetting scheme given in Example 1.

The result is shown in Table 3:

TABLE 3

| HRP-maleimide Calculated, mM | Maleimide groups measured, mM | Number of maleimide groups per enzyme |
|---|---|---|
| 0.0238 | 0.1965 | 8.26 |
| 0.0476 | 0.4760 | 10.00 |
| 0.0714 | 0.7600 | 10.64 |
| 0.0952 | 0.8000 | 8.40 |
| 0.1190 | 1.0150 | 8.53 |

This result clearly shows that the presence of protein does not interfere with the determination. The measurement is linear over a sufficiently large concentration range. The accuracy of the results is checked by determination of the number of primary amino groups before and after the reaction with heterocrosslinker. On average, 10 amino groups are used for bonding with the heterocrosslinker. Thus, the numerical values given by the two methods are in very good agreement. However, whereas the latter method enables bonded maleimide groups to be calculated via a laborious double determination of the primary amino groups, the novel method produces the same results in a shorter time. Moreover, the novel method is superior especially because it determines exclusively active maleimide groups, i.e., those capable of bonding with thiol groups.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for determining the number of functional reactive maleimide groups in a maleimide group-containing protein sample, comprising:

(a) reacting a protein sample containing maleimide groups with a reagent containing thiol groups;
   (b) reacting the resultant mixture with a chromogen or fluorogen which reacts with unreacted thiol groups; and
   (c) measuring the resultant intensity of light or fluorescence of the chromogen or fluorogen.

2. A method of claim 1, wherein a mercaptoalkanol is used as the reagent containing thiol groups.

3. A method of claim 2, wherein the mercaptoalkanol is mercaptoethanol.

4. A method of claim 1, wherein 2,2'-dinitro-5,5'-dithiodibenzoic acid is used as the chromogen.

5. A method of claim 2, wherein 2,2'-dinitro-5,5'-dithiodibenzoic acid is used as the chromogen.

6. A method of claim 1, wherein the protein is an antibody or antibody fragment.

7. A method of claim 1, wherein the measuring step is performed photometrically.

8. A method of claim 7, wherein the measuring step is performed at 436 nm.

* * * * *